US00PP08807P

United States Patent [19]

Polys

[11] Patent Number: Plant 8,807

[45] Date of Patent: Jun. 28, 1994

[54] CHRYSANTHEMUM PLANT NAMED SUNNY CHERIE

[75] Inventor: Susan M. Polys, Salinas, Calif.

[73] Assignee: Yoder Brothers, Inc., Barberton, Ohio

[21] Appl. No.: 62,257

[22] Filed: May 17, 1993

[51] Int. Cl.[5] ..... A01H 5/00

[52] U.S. Cl. ..... Plt./82.2

[58] Field of Search ..... Plt. 82.2, 82.3, 74.1

[56] References Cited

U.S. PATENT DOCUMENTS 4,616,099 10/1986 Sparkes ..... 47/58

OTHER PUBLICATIONS

Broertjes, et al., 1980, "A mutant of a mustant of a . . . Irradiation of progressive radiation-induced mutants in a mutaiton breeding programme with *Chrysanthemum morifolium*,", Euphytica 29:526–530.

Gosling, 1979, "The Chrysanthemum Manual-6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums The Year Round", Blanford Press, London, pp. 27–29, 320–327.

Chan, 1966, "Chrysanthemum and Rose Mutations induced by X-Rays", Am. Soc. Hort. Sci. Proc., pp. 613–620.

Broertjes, 1966, "Mutation breeding of Chrysanthemums", Euphytica, 15:156–162.

Dowrick et al., 1966, "The induction of mutations in Chrysanthemum using X-and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Sunny Cherie particularly characterized by its flat capitulum form; daisy capitulum type; yellow ray floret color, with bronzing buds and bronze overcast of the underside of the ray florets; diameter across face of capitulum of 35 to 44 mm when fully opened, when grown as a pinched spray pot mum; very floriferous, with excellent display of many small flowers; photoperiodic flowering response of 51 to 52 days after start of short days; plant height, with 13 to 14 long days after sticking unrooted cuttings, and with 0 to 1 applications of 2500 ppm B-9 SP, ranges from 23 to 25 cm when grown as a pinched pot mum with 4 cuttings in a 15 cm pot; branching pattern is spreading and prolific, each plant having 6 to 8 laterals after pinch; and recommended as a spray pot mum.

2 Drawing Sheets

The present invention comprises a new and distinct cultivar of Chrysanthemum, botanically known as *Dendranthema grandiflora*, and referred to by the cultivar name Sunny Cherie.

Sunny Cherie, identified as 4251 (89-114C03) is a product of a mutation induction program. The new cultivar was discovered and selected by Susan M. Polys on Jan. 13, 1992, in a controlled environment in Salinas, Calif., as one flowering plant within a flowering block established as rooted cuttings from stock plants which had been exposed as unrooted cuttings to an X-ray source of 1750 rads in Fort Myers, Fla., on May 23, 1991. The irradiation parent cultivar was an unnamed proprietary seedling identified as 4207 (89-114003), and described as a daisy spray pot mum with a flat capitulum form; a very light pink ray floret color; diameter across face of capitulum of 32 to 48 mm when fully opened, flowering response period of 49 to 56 days after start of short days; plant height of 18 to 25 cm with 0 to 1 applications of 2500 ppm B-9 SP when grown as a pinched pot mum in a 15 cm pot; and spreading and prolific branching pattern, with 6 to 8 laterals after pinch. The parent cultivar has not been sold or offered for sale, or otherwise publicly disclosed.

The irradiation program resulting in Sunny Cherie had as its primary objective the expansion of the color range of the parent seedling 4207, with the ray floret color of the parent considered to be too light for commercial introduction, while all other characteristics of the parent were considered to be excellent. The irradiation program comprised irradiating cuttings of the parent cultivar at irradiation levels of 1500, 1750 and 2000 rads. A total of 2470 cuttings harvested from a total of 225 irradiated plants were planted on Sep. 9, 1991. Of these, 37 initial selections were made, which selections were then revegetated and reflowered. Three consecutive flowerings resulted in discarding 32 of the original 37 selections on Jul. 1, 1992. Five selections were retained and reflowered again, ultimately resulting in the decision to introduce all remaining selections as Sunny Cherie, Dark Cherie, Honey Cherie, Soft Cherie and Sweet Cherie. Applications are pending for the other induced mutations.

The first act of asexual reproduction of Sunny Cherie was accomplished when vegetative cuttings were taken from the initial selection in Mar. 1992 in a controlled environment in Salinas, Calif., by technicians working under supervision of Susan M. Polys.

Horticultural examination of controlled flowerings of successive plantings has shown that the unique combination of characteristics as herein disclosed for Sunny Cherie are firmly fixed and are retained through successive generations of asexual reproduction.

Sunny Cherie has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Sunny Cherie, which, in combination, distinguish this Chrysanthemum as a new and distinct cultivar:

1. Flat capitulum form.
2. Daisy capitulum type.
3. Yellow ray floret color, with bronzing buds and bronze overcast of the underside of the ray florets.
4. Diameter across face of capitulum of 35 to 44 mm when fully opened, when grown as a pinched spray pot mum.
5. Very floriferous, with excellent display of many small flowers.
6. Photoperiodic flowering response of 51 to 52 days after start of short days.
7. Plant height, with 13 to 14 long days after sticking unrooted cuttings and with 0 to 1 applications of 2500 ppm B-9 SP, ranges from 23 to 25 cm when grown as a pinched pot mum with 4 cuttings in a 15 cm pot.
8. Branching pattern is spreading and prolific, each plant having 6 to 8 laterals after pinch.
9. Recommended as a spray pot mum.

The accompanying photographic drawings show typical inflorescence and leaf characteristics of Sunny Cherie, with the colors being as nearly true as possible with illustrations of this type.

Sheet 1 is a color photograph of a potted mum of Sunny Cherie, with 4 cuttings in a 15 cm pot.

Sheet 2 is a black and white photograph showing the upper and under sides of the leaves of the Cherie series at three stages of development (mature, intermediate and immature). In sheet 2 a measuring tape in centimeters has been added.

Of the commercial cultivars known to the inventor, the most similar in comparision to Sunny Cherie is the cultivar identified as Alouette, disclosed in U.S. Plant Pat. No. 7,468. Reference is made to attached Chart A, which compares certain characteristics of Sunny Cherie with the same characteristics as Alouette.

Similar traits are ray floret color, capitulum form and type, branching pattern and recommendation as a spray pot mom. Sunny Cherie has a larger diameter of capitulum than Alouette, and has a slower flowering response when grown side by side. The range of measurements of Alouette is much wider than the range of measurements of Sunny Cherie, based on the fact that Alouette has been tested for many years, while Sunny Cherie has been tested for only nine months at the time of the application.

When compared with the parent seedling, all traits of Sunny Cherie are similar to those of the parent, except for the color of the ray florets. When comparing the description of Sunny Cherie with the description of the parent, it is evident that the parent seedling has a much wider range of measurements than Sunny Cherie. This is also based on evaluations over a long time period for the parent in comparison with the short time period that Sunny Cherie was tested.

In the following description color references are made to The Royal Horticultural Society Colour Chart.

The color values were determined on plant material grown as a pinched spray pot mum in Salinas, Calif. on Feb. 23, 1993.

Classification:

*Botanical.*—*Dendranthema grandiflora* cv Sunny Cherie.

*Commercial.*—Flat daisy spray pot mum.

INFLORESCENCE

A. Capitulum:

*Form.*—Flat.

*Type.*—Daisy.

*Diameter across face.*—35 to 44 mm when fully opened.

B. Corolla of ray florets:

*Color (general tonality from a distance of three meters).*—Yellow with bronzing buds and bronze overcast of the underside of the ray florets.

*Color (upper surface).*—9B.

*Color (under surface).*—9B, overlaid with 167D.

*Shape.*—Straight, oblong, slightly ribbed.

C. Corolla of disc florets:

*Color (mature).*—14B.

*Color (immature).*—14B, center overlaid with 144B.

D. Reproductive organs:

*Androecium.*—Present on disc florets only; moderate pollen.

*Gynoecium.*—Present on boty ray and disc florets.

PLANT

A. General appearance:

*Height.*—23 to 25 cm when grown as a pinched pot mum with 13 to 14 long days prior to start of short days, with 0 to 1 applications of 2500 ppm B-9 SP.

*Branching pattern.*—Spreading and prolific, with 6 to 8 laterals after pinch.

B. Foliage:

*Color (upper surface).*—147A.

*Color (under surface).*—147B.

*Shape.*—See photograph.

CHART A

| CULTIVAR | SUNNY CHERIE | ALOUETTE |
|---|---|---|
| Ray floret color | Yellow with bronze buds and underside | Yellow with bronze buds and underside |
| Capitulum form and type | Flat Daisey | Flat Daisey |
| Diameter across face of capitulum | 35 to 44 mm | 32 to 38 mm |
| Flowering Response | 51 to 52 days | 45 to 52 days |
| Plant height with 13 to 14 long days | 23 to 25 cm | 20 to 28 cm |
| Branching pattern | Spreading 6 to 8 laterals | Spreading 6 to 8 laterals |
| Recommended as | Spray pot mum | Spray pot mum |

COMPARISONS MADE OF PLANTS GROWN AS PINCHED SPRAY POT MUMS IN SALINAS, CALIFORNIA

I claim:

1. A new and distinct Chrysanthemum plant named Sunny Cherie, as described and illustrated.

* * * * *

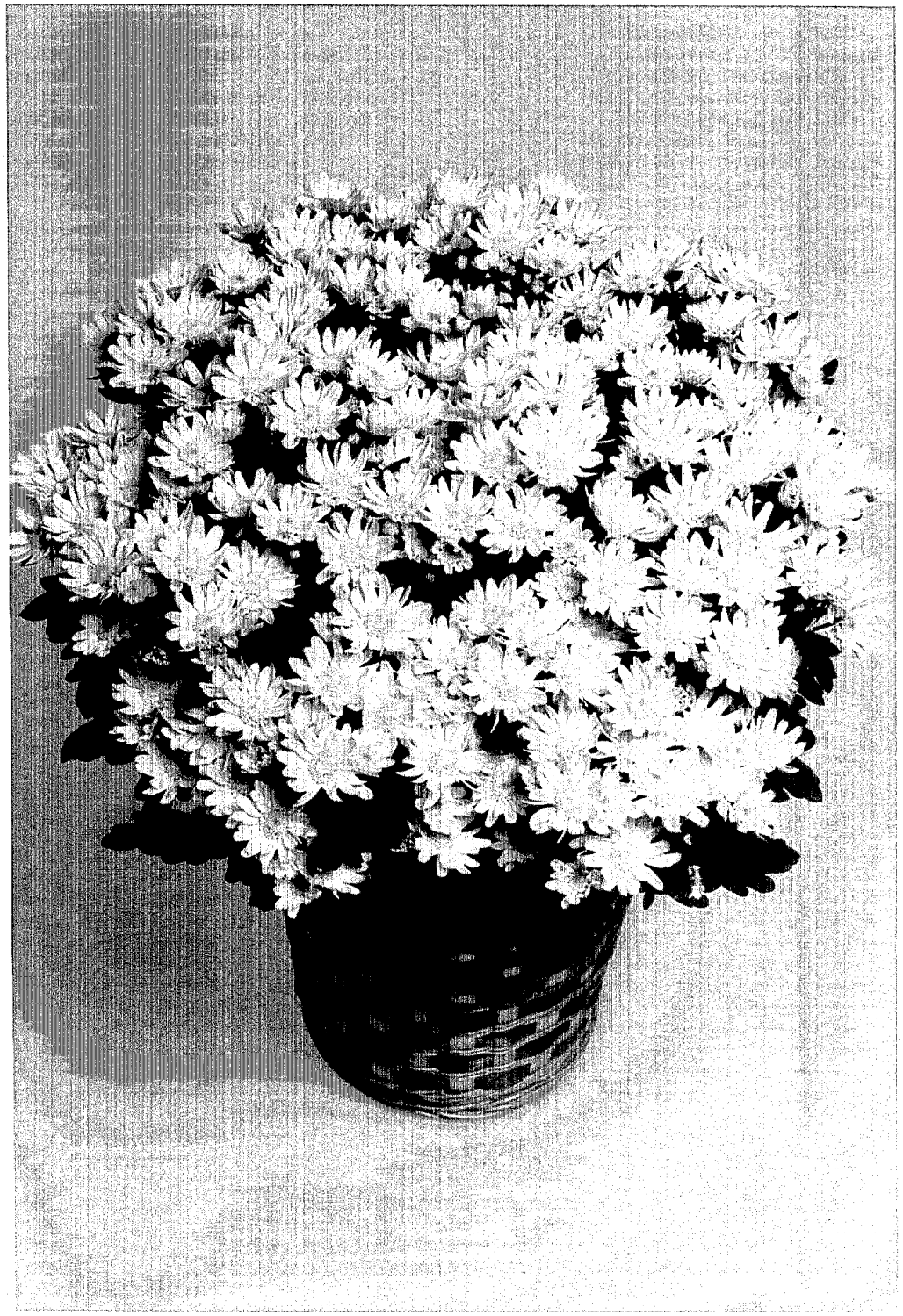

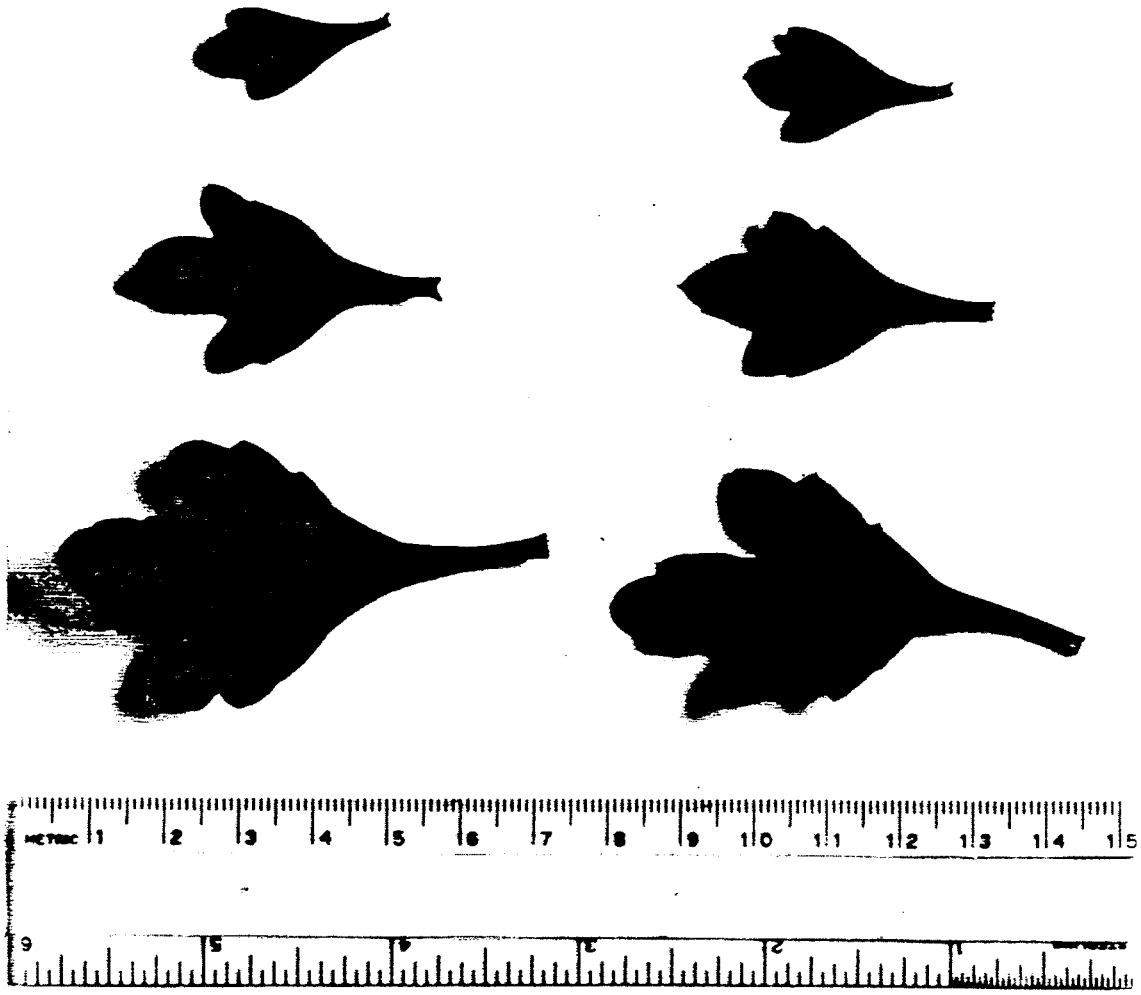
METRIC 1 2 3 4 5 6 7 8 9 10 11 12 13 14 15